US010167267B2

(12) United States Patent
Yi et al.

(10) Patent No.: US 10,167,267 B2
(45) Date of Patent: Jan. 1, 2019

(54) CONVERSION AND PURIFICATION OF BIOMASS

(71) Applicant: AGENCY FOR SCIENCE, TECHNOLOGY AND RESEARCH, Singapore (SG)

(72) Inventors: Guangshun Yi, Singapore (SG); Yugen Zhang, Singapore (SG)

(73) Assignee: AGENCY FOR SCIENCE, TECHNOLOGY AND RESEARCH, Singapore (SG)

(*) Notice: Subject to any disclaimer, the term of this patent is extended or adjusted under 35 U.S.C. 154(b) by 0 days.

(21) Appl. No.: 15/023,668

(22) PCT Filed: Sep. 17, 2014

(86) PCT No.: PCT/SG2014/000439
§ 371 (c)(1),
(2) Date: Mar. 21, 2016

(87) PCT Pub. No.: WO2015/041601
PCT Pub. Date: Mar. 26, 2015

(65) Prior Publication Data
US 2016/0207899 A1    Jul. 21, 2016

(30) Foreign Application Priority Data
Sep. 20, 2013  (SG) ................ 201307141-0

(51) Int. Cl.
*C07D 307/02*   (2006.01)
*C07D 307/68*   (2006.01)
(Continued)

(52) U.S. Cl.
CPC .......... *C07D 307/68* (2013.01); *B01J 23/007* (2013.01); *B01J 23/52* (2013.01); *B01J 23/66* (2013.01);
(Continued)

(58) Field of Classification Search
CPC ...... C07D 307/48; C07D 307/68; B01J 23/66; B01J 23/007; B01J 23/52; B01J 35/035; B01J 37/0013
(Continued)

(56) References Cited

U.S. PATENT DOCUMENTS 3,326,944 A      6/1967  Lew
2013/0150596 A1* 6/2013  Backes ............... C07D 307/46
                                               549/488

FOREIGN PATENT DOCUMENTS

GB        591858 A       9/1947
WO   WO 2013/101999 A1   7/2013
(Continued)

OTHER PUBLICATIONS

Gallo et al, Production and upgrading of 5-hydroxymethylfurfural using heterogeneous catalysts and biomass-derived solvents, Green Chem., 2013, 15, p. 85-90.*
(Continued)

*Primary Examiner* — Taylor V Oh
(74) *Attorney, Agent, or Firm* — Womble Bond Dickinson (US) LLP

(57) ABSTRACT

The present invention relates to a method for synthesizing an optionally substituted furoic acid by dehydrating a biomass and oxidizing the optionally substituted furan derived from the dehydration reaction. Water extraction has been incorporated as a step between the dehydration and the oxidation in order to purify the intermediate optionally substituted furan before having it oxidized. Prior to this water extraction, the organic solvent used for dehydration may be separated by evaporation. The provision of the water extraction allows impurities to be separated from the intermediate optionally substituted furan.

20 Claims, 8 Drawing Sheets

(51) Int. Cl.
   *B01J 23/52*     (2006.01)
   *C07D 307/48*    (2006.01)
   *B01J 37/03*     (2006.01)
   *B01J 23/00*     (2006.01)
   *B01J 23/66*     (2006.01)
   *B01J 35/00*     (2006.01)

(52) U.S. Cl.
   CPC ......... *B01J 35/0013* (2013.01); *B01J 37/035* (2013.01); *C07D 307/48* (2013.01)

(58) Field of Classification Search
   USPC ........................................................ 549/485
   See application file for complete search history.

(56) References Cited

FOREIGN PATENT DOCUMENTS

WO    WO 2013/146085 A1    10/2013
WO    WO 2014/058859 A2    4/2014

OTHER PUBLICATIONS

Gupta et al, Hydrotalcite-supported gold-nanoparticle-catalyzed highly efficient base-free aqueous oxidation of 5-hydroxymethylfurfural into 2,5-furandicarboxylic acid under atmospheric oxygen pressure, Green Chem., 2011, 13, p. 824-827.*

Y. Roman—Leshkov et al, Production of dimethylfurfuran for liquid fuels from biomass-derived carbonhydrates, Nature, 2007, 447, p. 982-985.*

Kuster, 5-hydroxymethylfurfural(HMF). A Review focusing on its manufacture, Starch/starke, 42, Nr. 8, p. 314-321. (Year: 1990).*

Office Action for counterpart Chinese Patent Application No. 201480063464.5 with English translation, 14 pgs., (May 26, 2017).

Sara E. Davis, et al., "Oxidation of 5-hydroxymethylfurfural over supported PT, Pd and Au catalysts," Catalysis Today. vol. 160, pp. 55-60 (2011).

PCT International Search Report for PCT Counterpart Application No. PCT/SG2014/000439, 5 pgs. (Dec. 8, 2014).

PCT Written Opinion for PCT Counterpart Application No. PCT/SG2014/000439, 10 pgs. (Dec. 8, 2014).

PCT International Preliminary Report on Patentability on PCT Application No. PCT/SG2014/000439, 22 pgs, (Jan. 28, 2016).

Dierk Martin, et al., "Versatile building blocks from disaccharides: Glycosylated 5-hydroxymethylfurfurals," Tetrahedron: Asymmetry, vol. 17, pp. 756-762 )2006).

MA Jiping, et al., "Advances in selective catalytic transformation of polyols to value-added chemicals," Chinese Journal of Catalysis, vol. 34, pp. 492-507 (2013).

R-J. Van Putten, at al., "Hydroxymethylfurfural, A Versatile Platform Chemical Made from Renewable Resources." Chemical Reviews, vol. 13, No. 3, pp. 1499-1597 (2013).

Martin Kroger, et al., "A new approach for the production of 2,5-furandicarboxylic acid by in situ oxidation of 5-hydroxymethylfurfural starting from fructose," Topics in Catalysis, vol. 13, pp. 237-242 (2000).

L. Rigel, et al., "Direct preparation of 5-hydroxymethyl-2-furancarboxaidehyde from polyholosides: a chemical valorisation of the Jerusalem artichoke (*Helianthus tuberosus*L.)," Biomass, vol. 3, Iss. 2, pp. 151-163 (1983).

Linke Lai, et al., "The production of 5-hydroxymethylfurfural from fructose in isopropyl alchohol; A green and efficient system," ChemSusChem, vol. 4, Iss. 12, pp. 1745-1748 (Dec. 16, 2011).

A. Villa, et al., "Pd-modified Au on carbon as an effective and durable catalyst for the direct oxidation of HMF to 2,5-furandicarboxylic acid," ChemSusChem, vol. 6, Iss. 4, pp. 609-612 (2013).

S. E. Davis, et al., "On the mechanism of selective oxidation of 5-hydroxymethylfurfural to 2,5-furandicarboxylic acid over supported Pt and Au catalysts," Green Chemistry, vol. 14, pp. 143-147 (2012).

Dr. Guangshun Yi, ei al., "Purification of Biomass-Derived 5-Hydroxymethylfurfural and Its Catalytic Conversion to 2,5-Furandicarboxylic Acid," ChemSusChem, vol. 7, Iss. 8, pp. 2131-2135 (Aug. 2014).

John P. Holdren, "Energy and Sustainability," Science, vol. 315, p. 737 (Feb. 9, 2007).

O.R. Inderwildi, et al., "Quo vadis biofuels?," Energy & Environmental Science, Issue 4, No. 2, pp. 343-346 (Apr. 1, 2009).

Yugen Zhang, et al., "Sustainable chemistry: imidazolium salts in biomass conversion and CO2 fixation," Energy & Environmental Science, Issue 4, pp. 408-417 (Mar. 1, 2010).

Alessandro Gandini, et al., "The furan counterpart of poly(ethylene terephthalate): An alternative material based on renewable resources." Journal of Polymer Science, Part A, Polymer Chemistry, vol. 47, Iss. 1, pp. 295-298 (Jan. 1, 2009).

Haibo Zhao, et al., "Metal Chlorides in Ionic Liquid Solvents Convert Sugars to 5-Hydroxymethylfurfural," Science, vol. 316, pp. 1597-1600 (Jun. 15, 2007).

Y. Roman-Leshkov, et al., "Solvent Effects on Fructose Dehydration to 5-Hydroxymethylfurfural in Biphasic Systems Saturated with Inorganic Salts," Topics in Catalysis, Issue 52, pp. 297-303 (2009).

Y. Roman-Leshkov, et al., "Phase Modifiers Promote Efficient Production of Hydroxymethylfurfural from Fructose," Science, vol. 312, pp. 1933-1937 (Jun. 30, 2006).

Juben N. Chheda, et al., "Liquid-Phase Catalytic Processing of Biomass-Derived Oxygenated Hydrocarbons to Fuels and Chemicals," Angewandte Chemie-International Edition, Iss. 46, pp. 7164-7183 (2007).

George W. Huber, et al., "Synergies between Bio- and Oil Refineries for the Production of Fuels from Biomass," Angewandte Chemie-International Edition, Iss. 46, pp. 7184-7201 (2007).

Joseph J. Bozell, "Connecting Biomass and Petroleum Processing with a Chemical Bridge," Science, vol. 329, Iss. 5991, pp. 522-523 (Jul. 30, 2010).

Joseph J. Bozell, et al., "Technology development for the production of biobased products from biorefinery carbohydrates—the US Department of Energy's "Top 10" revisited," Green Chemistry, Iss. 12, pp. 539-554 (2010).

S. Dutta, et al., "A Brief Summary of the Synthesis of Polyester Building-Block Chemicals and Biofuels from 5-Hydroxymethylfurfural," ChemPlusChem, vol. 77, Issue 4, pp. 259-272 (Apr. 2012).

T.F. Wang, et al., "Water-Compatible Lewis Acid-Catalyzed Conversion of Carbohydrates to 5-Hydroxymethylfurfural in a Biphasic Solvent System," Topics in Catalysis, vol. 55, Iss. 7, pp. 657-662 (Jul. 2012).

A.A. Roastella, et al., "5-Hydroxymethylfurfural (HMF) as a building block platform: Biological properties, synthesis and synthetic applications," Green Chemistry, Issue 4, pp. 754-793 (2011).

C. Moreau, et al., "Recent Catalytic Advances in the Chemistry of Substituted Furans from Carbohydrates and in the Ensuing Polymers," Topics in Catalysis, vol. 27, Issue 1-4, pp. 11-30 (Feb. 2004).

P. Vinke, et al., "The Dehydration of Fructose Towards 5-Hydroxymethylfurfural Using Activated Carbon as Adsorbent," Starch/Staerke, vol. 44, Iss. 3, pp. 90-96 (1992).

K.D.O. Vigier, et al., "Conversion of fructose and inulin to 5-hydroxymethylfurfural in sustainable betaine hydrochloride-based media," Green Chemistry, vol. 14, Iss. 2, pp. 285-189 (2012).

K. Shimizu, et al., "Enhanced production of hydroxymethylfurfural from fructose with solid acid catalysts by simple water removal methods," Catalysis Communications, vol. 10, Iss. 14, pp. 1849-1853 (Aug. 25, 2009).

M. L. Ribeiro, et al., "Cooperative effect of cobalt acetylacetonate and silica in the catalytic cyclization and oxidation of fructose to 2,5-furandicarboxylic acid," Catalysis Communications, vol. 4, Iss. 2, pp. 83-86 (Feb. 2003).

E. Taarning, et al., "Chemicals from Renewables: Aerobic Oxidation of Furfural and Hydroxymethylfurfural over Gold Catalysts," Chemsuschem 2008, 1, 75.

(56) References Cited

OTHER PUBLICATIONS

Edward L. Kunkes, et al., "Catalytic Conversion of Biomass to Monofunctional Hydrocarbons and Targeted Liquid-Fuel Classes," Science, vol. 322, No. 5900, pp. 417-421 (Oct. 17, 2008).

A.M. Ruppert, et al., "Hydrogenolysis Goes Bio: From Carbohydrates and Sugar Alcohols to Platform Chemicals," Angewandte Chemie-International Edition, vol. 51, Iss. 11, pp. 2564-2601 (Mar. 12, 2012).

B. N. Zope, et al., "Influence of Reaction Conditions on Diacid Formation During Au-Catalyzed Oxidation of Glycerol and Hydroxymethylfurfural," Topics in Catalysis, vol. 55, Issue 1-2, pp. 24-32 (Mar. 2012).

O. Casanova, et al., "Biomass into Chemicals: Aerobic Oxidation of 5-Hydroxymethyl-2-furfural into 2,5-Furandicarboxylic Acid with Gold Nanoparticle Catalysts," Chemsuschem, vol. 2, Iss. 12, pp. 1138-1144 (Dec. 21, 2009).

\* cited by examiner

CONVERSION AND PURIFICATION OF BIOMASS

CROSS-REFERENCE TO RELATED APPLICATIONS

This patent application is a U.S. National Phase Application under 35 U.S.C. §371 of International Application No. PCT/SG2014/000439, filed Sep. 17, 2014, entitled CONVERSION AND PURIFICATION OF BIOMASS, which claims priority to Singapore Patent Application No. 201307141-0, filed Sep. 20, 2013.

TECHNICAL FIELD

The present invention generally relates to a method for producing an optionally substituted furoic acid, such as 2,5-furandicarboxylic acid (FDCA), from a purified, optionally substituted furan, such as 5-hydroxymethylfurfural (HMF), obtained from a biomass. The present invention also relates to a method of purifying optionally substituted furans obtained from a biomass.

BACKGROUND

The depletion of fossil resources has generated interests in the development of renewable and sustainable alternatives for fuels and chemicals. Chemical industries are shifting their focus to the development of sustainable manufacturing processes by utilizing abundant biomass in environmentally benign solvent. In this context, optionally substituted furoic acids, such as 2,5-furandicarboxylic acid (FDCA), have received significant attention as a possible replacement for terephthalic acid for the production of polyamides, polyesters, and polyurethanes. For instance, a furan based polymer poly(ethylene-2,5-furandicarboxylate) (PEF) prepared from renewable sources demonstrated comparable thermal stability to polyethylene terephthalate (PET), a polymer commonly utilized in various applications related to consumer goods.

The FDCA derived from a biomass may be produced by aerobic oxidation of HMF using various suitable metal catalysts. Meanwhile, the HMF may be separately prepared by acid catalyzed dehydration of sugars or cellulose found in any biomass.

Conventionally, the oxidization of HMF to FDCA was simulated using commercially pure HMF and such studies are unlikely to demonstrate the direct conversion of fresh biomass-derived HMF into FDCA. Such simulations are also unlikely to integrate the acid catalysed dehydration and the metal catalysed oxidization as a single step process. The direct conversion of biomass to FDCA and the integration of dehydration and oxidation as a single step may not have been investigated most probably because HMF is already commercially available. Moreover, FDCA obtained from commercial HMF may not contain impurities as compared to HMF derived from actual biomass. Hence, the conversion of biomass-derived HMF to FDCA may not be as straight-forward as those simulated using commercial HMF.

When a biomass is used to produce FDCA or other furoic acids, impurities may be present. These impurities may remain after the carbohydrates in the biomass were dehydrated to produce HMF or any other optionally substituted intermediate furan. Consequently, these impurities may deleteriously affect downstream catalytic oxidation of the furan for producing furoic acids as the impurities tend to deposit on the catalyst surface causing deactivation. As HMF and similar furans are intermediate molecules and not the final product, it is not only crucial to optimize their synthesis process but also to develop an efficient isolation or purification method that may be integrated into any subsequent downstream reactions, such as the further catalytic oxidation to furoic acids e.g. FDCA. Only through such efforts may the direct conversion of biomass to FDCA become economically viable for large-scale production.

In a more recent study which describes a two-step process conversion of glucose to FDCA, HMF was produced using a biphasic system. Such biphasic system may require an aqueous reaction layer and an organic extracting layer comprising alcohols or ketones. Hence, multiple solvents may be required. The HMF obtained from such a biphasic system may be subsequently purified by distillation or multi-cycle extraction with cyclopentane as the extracting solvent. The HMF may be further oxidized to FDCA with $Au/TiO_2$ catalyst which was reported to achieve only about 80% yield. This also means that the overall yield for this two-step process has a low range of 35% to 50%. Based on this, the two-step conversion of FDCA from biomass-derived HMF remains economically unbeneficial.

Apart from a biphasic system, other methods, such as a single phase (mono-phase) dehydration system, have been developed to convert biomass to HMF. HMF may be produced from a mono-phase system by using solvents such as dimethyl sulfoxide, ionic liquids, tetrahydrofuran (THF), and γ-valerolactone (GVL). However, neither does this resolve the issues caused by impurities nor does it allow the integration of catalytic dehydration and catalytic oxidation to become possible.

One of the predominant impurities that may be present during the dehydration of HMF is humins. Humins may be soluble in many organic solvents and thus co-exist with HMF. The presence of humins adversely affects the appearance of the final product as well as downstream reactions when HMF is converted to other chemicals. To mitigate this, various methods such as organic extraction, column chromatography, high performance liquid chromatography (HPLC), and activated carbon absorbents, have been used to isolate and purify HMF. Conventional extraction methods typically involve multi-cycle processes that not only fail to alleviate the problems posed by humins which may dissolve readily in the extracting solvents along with the HMF but also consumes large amount of solvents. Hence, the resultant HMF obtained through such multi-cycle extractions may possess a dark brown colour instead of being an almost clear pale yellow solution which is characteristic of pure HMF solution. Although column or HPLC methods may generate high purity HMF, these methods may not be suitable for mass production. Likewise, activated carbon may be used to remove impurities from HMF solution but it also absorbs HMF. Hence, all these methods may not be cost-effective or suitable for mass production.

As mentioned above, impurities present along with HMF and other similar furans adversely affect the catalytic oxidization reaction. When such impurities, particularly humins, get deposited on the surface of the metal catalyst, deactivation of the catalyst occurs and the oxidation may not be able to proceed completely, thereby resulting, for instance, in a mixture of FDCA and 5-hydroxymethyl-2-furancarboxylic acid (HFCA), if unpurified HMF is oxidized.

There is therefore a need to provide a method of purifying HMF and other furans derived from biomass that overcomes, or at least ameliorates, one or more of the disadvantages described above.

There is also a need to provide a method which is capable of allowing the dehydration of biomass and the oxidation of the intermediate to be integrated.

Accordingly, such a method is capable of reducing the use of multiple solvents, addressing the problems posed by impurities that co-exist with HMF and serves as a cost effective means for the mass production of FDCA or other downstream products.

SUMMARY

In one aspect, there is provided a method for synthesizing an optionally substituted furoic acid, comprising:

converting a biomass to an optionally substituted furan via a dehydration reaction in the presence of an organic solvent;

purifying the optionally substituted furan by first partially or fully separating the organic solvent from the optionally substituted furan produced from said dehydration reaction, followed by extraction of the optionally substituted furan with water; and oxidizing the extracted optionally substituted furan to form the optionally substituted furoic acid.

The biomass may comprise a carbohydrate selected from cellulose, fructose, glucose or any other sugar. An example of such a biomass may be Jerusalem artichoke (JAT).

The organic solvent used for the dehydration reaction may be partially or fully separated by evaporation. This may enhance extraction of the optionally substituted furan or reduce the amount of water extraction needed to be able to fully extract the optionally substituted furan.

When the organic solvent is partially or fully evaporated, a solid residue or an aqueous slurry comprising the optionally substituted furan and the impurities may be obtained. These impurities may include any compounds that may exist after dehydration of the biomass. Examples may include humins and other polymers.

The water extraction may be repeated several times and the extracts containing the optionally substituted furan may be combined. By repeating the water extraction, the extraction yield of the optionally substituted furan, particularly HMF, may be increased. This water extraction may be repeated for 2 to 3 times.

To obtain the optionally substituted furan, the carbohydrates present in the biomass may have to undergo a dehydration reaction. This dehydration reaction may be an acid catalyzed dehydration reaction. An acid catalyst is used as it effectively leads to the formation of an optionally substituted furan. In certain instances, only an acid catalyst may work for this type of reaction. This acid catalyzed dehydration reaction may occur in the presence of a monophase solvent system or a biphasic solvent system. Regardless of the kind of solvent system used for dehydration, water extraction may be flexibly implemented.

The optionally substituted furan as disclosed herein may be unsubstituted or substituted by at least one —$C_1$-$C_{10}$-alkyl-OH, —C(=O)H (aldehyde) group or a combination of both. Where the optionally substituted furan comprises a -alkyl-OH substituent group, this -alkyl-OH substituent group may comprise any number of carbon atoms between 1 to 10. The optionally substituted furan may comprise at least one —$C_1$-$C_6$-alkyl-OH. Particularly, the optionally substituted furan may be 5-(hydroxymethyl)furfural. This HMF is a particularly useful intermediate product for producing downstream polymers or an optionally substituted furoic acid. This optionally substituted furoic acid may be unsubstituted or substituted by at least one —$C_1$-$C_{10}$-alkyl-OH, —COOH (carboxylic acid) group or a combination thereof. Where the optionally substituted furoic acid comprises a -alkyl-OH substituent group, this -alkyl-OH substituent group may comprise any number of carbon atoms between 1 to 10. Particularly, this optionally substituted furoic acid may be 2,5-furandicarboxylic acid (FDCA) or 5-hydroxymethyl-2-furancarboxylic acid (HFCA). This optionally substituted furoic acid may have the same number of carbon atoms as the optionally substituted furan from which it is derived.

The evaporated organic solvent may be selected from the group consisting of alcohols, ketones, tetrahydrofuran, γ-valerolactone and mixtures thereof. Particularly, the organic solvent may be selected from isopropanol, 1-butanol and methyl isobutyl ketone (MIBK). The organic solvent may solely comprise isopropanol. Advantageously, these solvents have low boiling points and thus evaporate more easily. If the organic solvents have high boiling points, it may become difficult to obtain the raw optionally substituted furan, such as the HMF. Organic solvents with boiling point above 50° C. may be used although organic solvents having a boiling point of 50° C. or less allow easier evaporation.

An ionic liquid may be added as a co-solvent for use in the dehydration reaction. This ionic liquid may be water. Water is an environmentally benign solvent as compared to other organic solvents, such as cyclopentane.

In order to obtain an optionally substituted furoic acid, the optionally substituted furan may have to be oxidized in the presence of oxygen, a catalytic system and optionally a base. If water extraction is not carried out prior to this oxidation, impurities that may be present with the optionally substituted furan may deposit on the catalyst surface and cause deactivation of the catalyst thereby resulting in incomplete oxidation. Lower yield and quality of the resultant optionally substituted furoic acid may also be obtained as a result of the presence of impurities.

The catalytic system used for this oxidation may be a supported catalytic system comprising gold/hydrotalcite (Au/HT), gold-palladium/hydrotalcite ($Au_8Pd_2$/HT) or platinum/carbon (Pt/C).

For optimum oxidation, catalytic oxidation may be first carried out for about 1 to 3 hours at about 30 to 70° C. The oxidation may then continue at a higher temperature of 80 to 110° C. for an additional 4 to 10 hours. This may help to aid complete oxidation. For instance, when HMF is the optionally substituted furan that is oxidized, some of it may be converted to HFCA. By increasing oxidation temperature and reaction time, this HFCA may be eventually converted to the desired FDCA so as to improve overall conversion yield.

In another aspect, there is provided an aqueous solution of 5-(hydroxymethyl)furfural obtainable by:

converting a biomass to an optionally substituted furan via a dehydration reaction in the presence of an organic solvent;

purifying the optionally substituted furan by first partially or fully separating the organic solvent from the optionally substituted furan produced from said dehydration reaction, followed by extraction of the optionally substituted furan with water.

As mentioned above, the organic solvent may be partially or fully separated by evaporation so as to obtain a solid residue or an aqueous slurry comprising the optionally substituted furan and/or the impurities found in the biomass.

Water may then be added to extract the optionally substituted furan, particularly the HMF. This water extraction may be repeated several times and the extracts containing the optionally substituted furan may be combined.

In another aspect, there is provided the use of the aqueous solution as defined above to convert 5-(hydroxymethyl)furfural to 2,5-furandicarboxylic acid by catalytic oxidation. To do so, catalytic oxidation of this aqueous solution may be carried out in the presence of oxygen, a catalytic system and optionally a base, wherein the catalytic system may be a supported catalytic system comprising gold/hydrotalcite, gold-palladium/hydrotalcite or platinum/carbon.

DEFINITIONS

The following words and terms used herein shall have the meaning indicated:

The term 'alkyl', as a group or part of a group, may be a straight or branched aliphatic hydrocarbon group. The alkyl may be a $C_1$-$C_{10}$ alkyl group. The alkyl may also contain any number of carbon atoms in the range of 1 to 10. Straight and branched $C_1$-$C_{10}$ alkyl substituents may be selected from the group consisting of methyl, ethyl, propyl, butyl, pentyl, hexyl, heptyl, octyl, nonyl, decyl and any isomers thereof. The alkyl may be selected from the group consisting of methyl, n-ethyl, n-propyl, 2-propyl, n-butyl, sec-butyl, iso-butyl, tert-butyl, n-pentyl, 3-methyl-1-butyl, 2-methyl-1-butyl, 2,2,-dimethyl-1-propyl, 3-pentyl, 2-pentyl, 3-methyl-2-butyl and 2-methyl-2-butyl. The alkyl may be a bridging group linked to the hydroxyl group.

The term "alkenyl group" includes within its meaning monovalent ("alkenyl") and divalent ("alkenylene") straight or branched chain unsaturated aliphatic hydrocarbon groups having from 2 to 10 carbon atoms, eg, 2, 3, 4, 5, 6, 7, 8, 9, or 10 carbon atoms and having at least one double bond, of either E, Z, cis or trans stereochemistry where applicable, anywhere in the alkyl chain. Examples of alkenyl groups include but are not limited to ethenyl, vinyl, allyl, 1-methylvinyl, 1-propenyl, 2-propenyl, 2-methyl-1-propenyl, 2-methyl-1-propenyl, 1-butenyl, 2-butenyl, 3-butentyl, 1,3-butadienyl, 1-pentenyl, 2-pententyl, 3-pentenyl, 4-pentenyl, 1,3-pentadienyl, 2,4-pentadienyl, 1,4-pentadienyl, 3-methyl-2-butenyl, 1-hexenyl, 2-hexenyl, 3-hexenyl, 1,3-hexadienyl, 1,4-hexadienyl, 2-methylpentenyl, 1-heptenyl, 2-heptentyl, 3-heptenyl, 1-octenyl, 1-nonenyl, 1-decenyl, and the like.

"Alkynyl" as a group or part of a group means an aliphatic hydrocarbon group containing a carbon-carbon triple bond and which may be straight or branched having from 2 to 10 carbon atoms or any number of carbon atoms falling within this range, in the normal chain. Exemplary structures include, but are not limited to, ethynyl and propynyl. The group may be a terminal group or a bridging group.

The term "cycloalkyl" as used herein refers to cyclic saturated aliphatic groups and includes within its meaning monovalent ("cycloalkyl"), and divalent ("cycloalkylene"), saturated, monocyclic, bicyclic, polycyclic or fused polycyclic hydrocarbon radicals having from 3 to 10 carbon atoms, eg, 3, 4, 5, 6, 7, 8, 9, or 10 carbon atoms. Examples of cycloalkyl groups include but are not limited to cyclopropyl, 2-methylcyclopropyl, cyclobutyl, cyclopentyl, 2-methylcyclopentyl, 3-methylcyclopentyl, cyclohexyl, and the like.

"Cycloalkenyl" means a non-aromatic monocyclic or multicyclic ring system containing at least one carbon-carbon double bond and possibly having from 5 to 10 carbon atoms per ring. Exemplary monocyclic cycloalkenyl rings include cyclopentenyl, cyclohexenyl or cycloheptenyl. The cycloalkenyl group may be substituted by one or more substituent groups. The group may be a terminal group or a bridging group.

The term "heterocycloalkyl" as used herein, includes within its meaning monovalent ("heterocycloalkyl") and divalent ("heterocycloalkylene"), saturated, monocyclic, bicyclic, polycyclic or fused hydrocarbon radicals having from 5 to 10 ring atoms wherein 1 to 5 ring atoms are heteroatoms selected from O, N, NH, or S. Examples include pyrrolidinyl, piperidinyl, quinuclidinyl, azetidinyl, morpholinyl, tetrahydrothiophenyl, tetrahydrofuranyl, tetrahydropyranyl, and the like.

"Alkynyloxy" refers to an alkynyl-O— group in which alkynyl is as defined herein. Alkynyloxy groups may be $C_1$-$C_{10}$ alkynyloxy groups or have any number of carbon atoms falling within this range. The group may be a terminal group or a bridging group. If the group is a terminal group it is bonded to the remainder of the molecule through the oxygen atom.

The term "halo" as used herein refers to a halogen substituent group represented by chlorine, fluorine, bromine or iodine. The terms for each of these "halo" substituent groups are chloro, fluoro, bromo or iodo, respectively.

"Haloalkyl" refers to an alkyl group as defined herein in which one or more of the hydrogen atoms has been replaced with a halogen atom selected from the group consisting of fluorine, chlorine, bromine and iodine. A haloalkyl group typically has the formula $C_nH_{(2n+1-m)}X_m$ wherein each X is independently selected from the group consisting of F, Cl, Br and I. In groups of this type n is typically from 1 to 10, or any number falling within this range. m may be 1 to 6 or any number falling within this range. Examples of haloalkyl include fluoromethyl, difluoromethyl and trifluoromethyl.

"Haloalkynyl" refers to an alkynyl group as defined herein in which one or more of the hydrogen atoms has been replaced with a halogen atom independently selected from the group consisting of F, Cl, Br and I.

The term "alkoxy" as used herein refers to straight chain or branched alkyloxy groups. Examples include methoxy, ethoxy, n-propoxy, isopropoxy, tert-butoxy, and the like.

"Alkenyloxy" refers to an alkenyl-O— group in which alkenyl is as defined herein. Alkenyloxy groups may comprise are $C_1$-$C_{10}$ alkenyloxy groups. The group may be a terminal group or a bridging group. If the group is a terminal group it is bonded to the remainder of the molecule through the oxygen atom.

The term "optionally substituted" as used herein means the group to which this term refers may be unsubstituted, or may be substituted with one or more groups independently selected from —$C_1$-$C_{10}$-alkyl, —$C_1$-$C_{10}$-alkenyl, —$C_1$-$C_{10}$-alkynyl, —$C_3$-$C_{10}$-cycloalkyl, —$C_5$-$C_{10}$-cycloalkenyl, —$C_5$-$C_{10}$-heterocycloalkyl having 1 to 5 hetero atoms selected from N, O and S in the ring, halo, —$C_1$-$C_{10}$-haloalkyl, —$C_1$-$C_{10}$-haloalkynyl, —$C_1$-$C_{10}$-alkoxy, —$C_1$-$C_{10}$-alkenyloxy, —$C_1$-$C_{10}$-haloalkoxy, —$C_1$-$C_{10}$-haloalkenyloxy, —$C_1$-$C_{10}$-alkyl-OH, —COOH carboxyl group, —COO$^-$Y$^+$ carboxylate group or a —C(=O)H aldehyde group, wherein Y$^+$ refers to any singly charged cation e.g. any group 1 metals.

The word "phase" as used herein refers to the phase of the solvent system used for the dehydration reaction. If the solvent system solely comprises an organic layer or an aqueous layer for the dehydration reaction to take place, then it may be taken that this solvent system has a single phase. In another instance, if the system employs an organic solvent and an aqueous solvent, such as water and alcohol, which are miscible with each other and capable of existing as a single phase for the dehydration reaction to take place, then such a system comprising two miscible solvents may also be considered as a single phase (mono-phase) system.

If a solvent system comprises an aqueous layer and an organic layer that are immiscible with each other, wherein only the aqueous phase serves as the reaction layer for the production of an optionally substituted furan from a carbohydrate, such a solvent system may be taken as a biphasic system.

The word "substantially", when used in the present disclosure, does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

DISCLOSURE OF OPTIONAL EMBODIMENTS

Exemplary, non-limiting embodiments of the present disclosure will now be disclosed.

Generally, there is a method for synthesizing a monomer, comprising:
(i) chemically converting a feedstock to an intermediate substance;
(ii) purifying said intermediate substance; and
(iii) chemically converting said intermediate substance to said monomer.

The feedstock may be a saccharide or biomass. The saccharide may be a sugar or cellulose, in which the sugar may be glucose or fructose. As for the biomass, it may be Jerusalem artichoke. The intermediate substance may be 5-(hydroxymethyl)furfural (HMF). The monomer may be 2,5-furandicarboxylic acid (FDCA).

The chemical conversion in (i) may refer to an acid catalyzed dehydration which means that this dehydration reaction may be carried out in the presence of an acid. This dehydration reaction may also be carried out via a single phase or biphasic solvent system. A particular acid used for such dehydration reaction may be hydrochloric acid.

Meanwhile, the single phase or biphasic system may comprise at least a solvent selected from the group consisting of an aqueous solvent, an organic solvent or their combination thereof. When the dehydration reaction occurs via a single phase system, the solvent may be selected from the group consisting of water, dimethyl sulfoxide, ionic liquids, isopropanol, tetrahydrofuran or γ-valerolactone. When the dehydration reaction occurs via a biphasic system, the two solvents used for such a system may be selected from the group consisting of water, sodium chloride, alcohols, ketones, or any of the solvents as described above. In a biphasic system, one of the two solvents may comprise an ionic liquid or an organic solvent.

In a biphasic system, the aqueous solvent may serve as the reaction layer, particularly for the dehydration reaction, and the organic solvent may serve as the extraction layer.

With regards to (ii), the purification comprises solvent evaporation and water extraction. The solvent that evaporates may be the organic solvent. This organic solvent may be partially or fully evaporated prior to carrying out the water extraction. Step (ii) may further comprise the addition of water after the partial or full evaporation of the organic solvent.

As for step (iii), the chemical conversion may refer to catalytic oxidation of the intermediate substance purified from step (ii) in order to obtain the monomer. This catalytic oxidation may be carried out in the presence of oxygen, a catalytic system and optionally a base. The catalytic system may be a supported catalytic system comprising gold/hydrotalcite, gold-palladium/hydrotalcite or platinum/carbon. The catalytic system may also comprise any metal catalyst with or without support. The base used for the catalytic oxidation system may be any suitable base. Some examples may include sodium hydroxide or sodium carbonate.

The catalytic oxidation may be first carried out for 2 hours at 50° C. and further carried out for 7 hours at 95° C. after the first 2 hours of oxidation.

The method as described above may be use to provide a monomer for use in the production of a polymer.

The above method may generally be used for obtaining 5-(hydroxymethyl)furfural, comprising:
(i) chemically converting a feedstock to 5-(hydroxymethyl)furfural;
(ii) purifying the 5-(hydroxymethyl)furfural from (i) by first separating an organic solvent from the product of (i), followed by extraction of 5-(hydroxymethyl)furfural with water.

The organic solvent may be partially or fully evaporated before the extraction with water in this instance. The evaporated organic solvent may be selected from alcohols, dimethyl sulfoxide, tetrahydrofuran, γ-valerolactone or ketones, or mixtures of them with other organic solvents. Examples of such alcohols may comprise isopropanol or 1-butanol and examples of ketones may comprise methyl isobutyl ketone.

The organic solvent may be solely isopropanol or a mixture of isopropanol with other organic solvents.

The feedstock for chemical conversion to HMF may be as described above. This chemical conversion in (i) may be an acid catalyzed dehydration. This conversion may be performed in a reaction solution comprising an organic solvent as described above. The chemical conversion in (i) may additionally comprise water as the solvent of the reaction solution.

A purified aqueous solution of 5-(hydroxymethyl)furfural may be obtained based on the above method as described. This aqueous solution of 5-(hydroxymethyl)furfural may be converted to 2,5-furandicarboxylic acid by catalytic oxidation which may occur in the presence of oxygen, a catalytic system and optionally a base. As described above, the catalytic system may be a supported catalytic system comprising gold/hydrotalcite, gold-palladium/hydrotalcite or platinum/carbon.

In accordance with the above, there is provided a method for synthesizing an optionally substituted furoic acid, comprising:

converting a biomass to an optionally substituted furan via a dehydration reaction in the presence an organic solvent;

purifying the optionally substituted furan by first partially or fully separating the organic solvent from the optionally substituted furan produced from said dehydration reaction, followed by extraction of the optionally substituted furan with water; and oxidizing the extracted optionally substituted furan to form the optionally substituted furoic acid.

The biomass used in the present method may be any biomass suitable for producing an optionally substituted furan or an optionally substituted furoic acid. Such a biomass may comprise carbohydrates which may be any saccharide selected from cellulose, fructose, glucose and any other sugars. An example of a suitable biomass may be Jerusalem artichoke (JAT). A biomass as described above may also contain various impurities, one of which may be humins. This dark coloured humin may be highly soluble in isopropanol or other organic solvents e.g. MIBK, THF and DMSO but may be insoluble in water.

The optionally substituted furan may refer to one that is unsubstituted or one that is substituted by at least one —$C_1$-$C_{10}$-alkyl-OH, —C(=O)H (aldehyde) group or a combination of either of these groups. If the optionally substituted furan happens to comprise —$C_1$-$C_{10}$-alkyl-OH, it may be an -alkyl-OH group comprising any number of carbon atoms from 1 to 10. The optionally substituted furan may comprise a —$C_1$-$C_6$-alkyl-OH substituent group. Such an optionally substituted furan may be one that is soluble in water. Such an optionally substituted furan may be 5-(hydroxymethyl)furfural (HMF). An optionally substituted furan as described above may be derived from any biomass by dehydrating the carbohydrates. This optionally substituted furan may co-exist with various impurities, including humins or other polymers. Since the optionally substituted furan may be soluble in both water and organic solvents, water extraction may be an effective method to isolate such an optionally substituted furan from these impurities. As shown in FIG. 1, the left vial contains a dark coloured HMF solution derived from a biomass after dehydrating the fructose in isopropanol (it should be noted that this crude HMF solution may have a dark brown colour). As mentioned above, the humin impurities may be soluble in isopropanol. When these impurities dissolve in isopropanol, the colour of the solution may become dark brown. Precipitates may or may not form in the isopropanol solution. The dark colour (brown) may be attributed to impurities which may be found in any of abovementioned biomass. These impurities are namely humins and other polymers. On the other hand, pure HMF solution may have a clear pale yellow color (right vial of FIG. 1).

After evaporation of the isopropanol, a viscous liquid may be obtained (see center vial of FIG. 1, it should be noted that this thick viscous residue may be black in colour). According to the findings as disclosed herein, it has been found that HMF and similar furans readily dissolve in water but not the impurities. It should be further noted that water present in excess during the dehydration reaction may cause HMF and the similar furans to convert to levulinic acid. Hence, the use of water in excess tends to be typically minimized or avoided.

However, after the optionally substituted furans and/or HMF are formed and the organic solvent has evaporated, it is possible to add water for extraction since the water added at this stage does not cause the furans or HMF to form levulinic acid. Therefore, water may be added for extraction to first form a transparent solution (It should be noted that when water is added, the solution may turn yellow due to HMF). According to the findings of the present disclosure, most of the impurities remained at the bottom of the vial (see right vial of in the bottom (FIG. 1a). Accordingly, this water extraction process is very efficient since 99% of the HMF may be recovered within two rounds of extraction (see FIG. 2).

As for the optionally substituted furoic acid, it may refer to one that is unsubstituted or one that is substituted by at least one —$C_1$-$C_{10}$-alkyl-OH, —COOH (carboxylic acid) group, or a combination of either of these groups among other potential substituents. If the optionally substituted furoic acid happens to comprise —$C_1$-$C_{10}$-alkyl-OH, it may be an -alkyl-OH group comprising any number of carbon atoms from 1 to 10. This optionally substituted furoic acid may comprise —$C_1$-$C_6$-alkyl-OH. Such an optionally substituted furoic acid may be 2,5-furandicarboxylic acid (FDCA) or 5-hydroxymethyl-2-furancarboxylic acid (HFCA), in which both compounds may be derived by oxidizing the optionally substituted furan, particularly HMF. This optionally substituted furoic acid may have the same number of carbons atoms as the optionally substituted furan from which it is derived.

In the present method, the organic solvent used for dehydration may be partially or fully separated by evaporation before adding water for extracting the optionally substituted furan. Alternatively, water may be added before evaporation of the organic solvent begins.

When the organic solvent is fully evaporated, a solid residue or an aqueous slurry comprising the optionally substituted furan and the various impurities may remain. When the organic solvent is partially evaporated, a solid residue or an aqueous slurry comprising the optionally substituted furan and the various impurities may remain. Regardless of whether a solid residue or an aqueous slurry remains after evaporating the dehydration solvent, water may be added to extract the optionally substituted furan. This aqueous solution comprising the optionally substituted furan may be centrifuged or filtrated to remove any impurities. Both the supernatant and the residue may be collected separately. Once separated, water may be added to the residue to extract any optionally substituted furan that remains. Similarly, this aqueous solution undergoes centrifugation or filtration and the supernatant containing the optionally substituted furan may be separated from the residue. This extraction process using water may be repeated several times and the extracts containing the optionally substituted furan, particularly the HMF, may be combined. In order to fully extract the optionally substituted furan, the water extraction may be repeated for 2 to 3 times or at least once.

The dehydration reaction as mentioned above used for deriving an optionally substituted furan from a biomass may be an acid catalyzed dehydration reaction. The acid used in such dehydration reaction may be any acid suitable for aiding the conversion of a sugar into an optionally substituted furan. Such acids may comprise hydrochloric acid, sulphuric acid, any mineral acids or any organic acids.

This acid catalyzed dehydration reaction may utilize a mono-phase solvent system or a biphasic solvent system.

In a single or mono-phase solvent system, one solvent phase may be used during the dehydration reaction. This solvent phase may comprise one or more solvents. Such solvents may be any solvent suitable for carrying out the dehydration reaction. This dehydration solvent may be selected from the group consisting of water, dimethyl sulfoxide, ionic liquids, isopropanol, tetrahydrofuran or γ-valerolactone. Where the solvent system comprises water and isopropanol, this solvent system may be classified as a single phase system since these liquids are miscible at any ratio. Water may be added before or during dehydration for the purpose of obtaining a higher HMF yield. As long as the amount of water remains insignificant compared to the alcohol solvent, the presence of water is unlikely to affect the dehydration reaction. Even if no water is added, HMF may be produced with a yield higher than 70%. Accordingly, the amount of water added before or during dehydration should not exceed 10% (by volume) of the reaction mixture in order to avoid formation of side products such as levulinic acid. If any water is present in the system before water extraction commences, for example, a mono-phase solvent system comprising isopropanol and water, both the water and the isopropanol solvent may be evaporated partially or completely before conducting the extraction using water. The solvent may also comprise alcohols, ketones or any other organic solvents. The solvent system may be a mixture of any of the abovementioned solvents as long as the system comprises a single phase for a mono-phase dehydration system.

In a biphasic solvent system, there may be an aqueous phase and an organic phase. The aqueous phase may serve as the reaction phase for the dehydration reaction. The organic phase may serve as the extracting phase for the optionally substituted furan. The aqueous phase may comprise of any one or more solvents suitable for use as the aqueous phase. Some examples include water, sodium chloride or any other ionic liquids. The organic phase may comprise any one or more organic solvents suitable for use as the organic phase. This organic solvent may be selected from the group consisting of ionic liquids, alcohols, ketones, tetrahydrofuran, γ-valerolactone and mixtures thereof. The alcohol may comprise isopropanol or 1-butanol and the ketone may be methyl isobutyl ketone (MIBK).

Other ionic liquids that are non-organic in nature may also be used as a solvent for the dehydration reaction regardless of whether a mono-phase or biphasic phase is utilized. An example of such an ionic liquid may be aqueous sodium chloride or water.

Accordingly, the evaporated organic solvent may be selected from the group consisting of dimethyl sulfoxide, ionic liquids, alcohols, ketones, tetrahydrofuran, γ-valerolactone and mixtures thereof. The evaporated organic solvent may be further selected from isopropanol, 1-butanol and methyl isobutyl ketone (MIBK). The evaporated organic solvent may solely comprise isopropanol.

The advantage of using an alcohol as the organic solvent for the dehydration reaction is because it may be an easy-to-use reaction media that is both environmentally friendly and cost efficient as alcohol is a volatile solvent that evaporates easily. Their capacity to dissolve sugar may also be higher compared to other organic solvents. Alcohol may also reversibly react with the optionally substituted furan, such as HMF, to form HMF ethers. This may prevent the decomposition or oligomerization of HMF.

In some instances, an ionic liquid may be used as a co-solvent in the dehydration reaction regardless of whether the solvent system is mono-phasic or biphasic. This ionic liquid may be water. This water may also serve to dissolve the acid catalyst.

After dehydrating the biomass and purifying the optionally substituted furan, the latter may be oxidized in the presence of oxygen, a catalytic system and optionally a base. Such a catalyst may be any catalyst suitable for carrying out the oxidation reaction. The catalyst may a metal catalyst with or without support. Some examples of suitable supported catalytic system comprise gold/hydrotalcite (Au/HT), platinum/carbon (Pt/C) or gold-palladium/hydrotalcite ($Au_8Pd_2$/HT). Other kinds of catalyst which may be suitable for this catalytic oxidation may comprise any supported Au and/or Pt catalyst, such as $Au/TiO_2$, $Au/CeO_2$, Pt/C, $Pt/TiO_2$ etc. This catalytic oxidation may be carried out for at least 20 hours. This catalytic oxidation may also be carried out for less than 20 hours. For optimum conditions, the oxidation may be first carried out for about 1 to 3 hours at about 30 to 70° C. followed by raising the temperature to 80 to 110° C. for another 4 to 10 hours. The first part of oxidation may also have a temperature falling within the range of about 30 to 60° C., 30 to 50° C., 30 to 40° C., 40 to 70° C., 50 to 70° C. or 60 to 70° C. The second part of oxidation may also have a temperature falling within the range of about 80 to 100° C., about 80 to 90° C., 90 to 110° C. or 100 to 110° C. To further illustrate, the oxidation reaction may be carried out at 50° C. for an initial period of 2 hours followed by increasing the temperature to 95° C. and continuing the oxidation reaction for a subsequent 7 hours at this higher temperature.

The base used for oxidation may be sodium hydroxide, sodium carbonate or any other suitable bases. When such a base is used with a hydrotalcite (HT) catalyst, leaching of magnesium ions from the HT support may be avoided since the FDCA may be neutralized by the base instead of reacting with the HT material. Optionally, a molar equivalent of base may be added in order to neutralized the FDCA acid and protect HT from dissolving. Other amounts of base may also be selected for addition to prevent HT from being reacted away.

If water extraction is not carried out after evaporation, oxidation of the optionally substituted furan to an optionally substituted furoic acid may yield a mixture of HFCA and FDCA (overall conversion yield may be less than 35%). This is because the presence of impurities may deactivate the catalyst resulting in incomplete oxidation.

On the other hand, if water extraction has been carried out according to the present method, the optionally substituted furan may be oxidized to yield to an optionally substituted furoic acid which solely comprises FDCA with an achievable yield of at least 98%.

In accordance with the method disclosed above, an aqueous solution of 5-(hydroxymethyl)furfural may be obtained by:

converting a biomass to an optionally substituted furan via a dehydration reaction in the presence of an organic solvent;

purifying the optionally substituted furan by first partially or fully separating the organic solvent from the optionally substituted furan produced from said dehydration reaction, followed by extraction of the optionally substituted furan with water.

The biomass may be any biomass as described above. Such a biomass is capable of serving as a suitable renewable alternative for producing polymers used in consumer goods.

The optionally substituted furan may refer to one that is unsubstituted or one that is substituted by at least one —$C_1$-$C_{10}$-alkyl-OH, —C(=O)H (aldehyde) group or a combination of either of these groups among other substituents. If the substituent group happens to comprise —$C_1$-$C_{10}$-alkyl-OH, it may be an alkyl-OH group comprising any number of carbon atoms from 1 to 10. Such an optionally substituted furan is soluble in water. Such an optionally substituted furan may be 5-(hydroxymethyl)furfural (HMF). An optionally substituted furan as described above may be derived from any biomass by dehydrating the carbohydrates. This optionally substituted furan may co-exist with various impurities, including humins. This optionally substituted furan may be soluble in both organic and aqueous solvents.

The optionally substituted furoic acid may refer to one that is unsubstituted or one that is substituted by at least one —$C_1$-$C_{10}$-alkyl-OH, —COOH (carboxylic acid) group, or a combination of either of these groups among other possible substituents. If the substituent group happens to comprise —$C_1$-$C_{10}$-alkyl-OH, it may be an -alkyl-OH group comprising any number of carbon atoms from 1 to 10. Such an optionally substituted furoic acid may be 2,5-furandicarboxylic acid (FDCA) or 5-hydroxymethyl-2-furancarboxylic acid (HFCA), in which both compounds may be derived by oxidizing the optionally substituted furan, particularly HMF.

As described above, the organic solvent may be partially or fully separated by evaporation. The organic solvent may be partially or fully evaporated to obtain a solid residue or an aqueous slurry. Once the organic solvent used in the dehydration reaction has evaporated, water may then be added to extract the optionally substituted furan, particularly the HMF from the impurities present in the biomass. This water extraction may be repeated several times as described above and the extracts containing the optionally substituted furan may be combined.

In accordance with the above, there is provided the use of the aqueous solution as defined above to convert 5-(hydroxymethyl)furfural to 2,5-furandicarboxylic acid by catalytic oxidation. To reiterate, this catalytic oxidation may be carried out in the presence of oxygen, a catalytic system and optionally a base, wherein the catalytic system may be a supported catalytic system comprising gold/hydrotalcite (Au/HT), gold-palladium/hydrotalcite ($Au_8Pd_2$/HT) or platinum/carbon (Pt/C).

BRIEF DESCRIPTION OF DRAWINGS

The accompanying drawings illustrate a disclosed embodiment and serve to explain the principles of the disclosed embodiment. It is to be understood, however, that the drawings are designed for purposes of illustration only, and not as a definition of the limits of the invention.

DETAILED DESCRIPTION OF DRAWINGS

Figure 3:
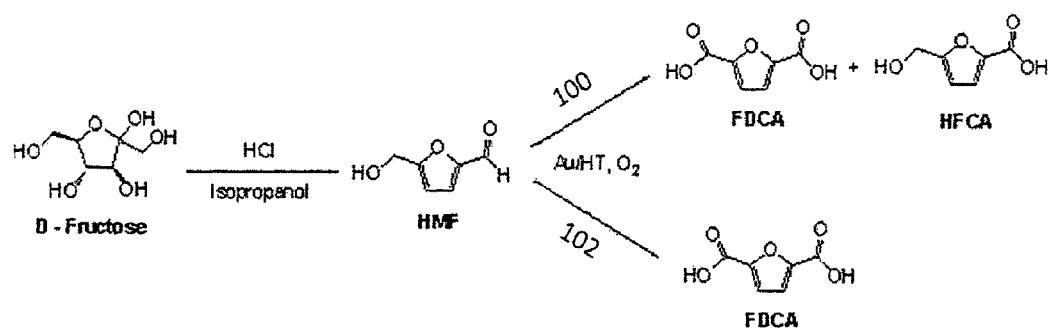
FIG. 3 depicts an integrated process for the conversion of fructose to FDCA.

FIG. 3 depicts an integrated process for the conversion of fructose to FDCA. In this process, D-fructose was first dissolved in isopropanol. Hydrochloric acid was then added as a catalyst for the dehydration reaction to form HMF. The HMF obtained after dehydration was then separated into two equivalent portions.

Using the first portion, the HMF was not purified and undergoes oxidation in the presence of oxygen and Au/HT catalyst. Step 100 depicts the pathway for producing FDCA using this unpurified HMF. Consequently, a mixture of 5-hydroxymethyl-2-furancarboxylic acid (HFCA) and FDCA was obtained as the final product. The FDCA yield was less than 35%.

As for the second portion, the HMF was purified via extraction with water. The purified extracts were then combined. The combined extracts are then subjected to the same oxidation step as described above. Step 102 depicts the pathway for producing FDCA using this purified HMF extracts. Consequently, only FDCA was obtained as the final product. The FDCA yield was about 98%. This means that the overall conversion yield was improved to about 83%.

Figure 16:
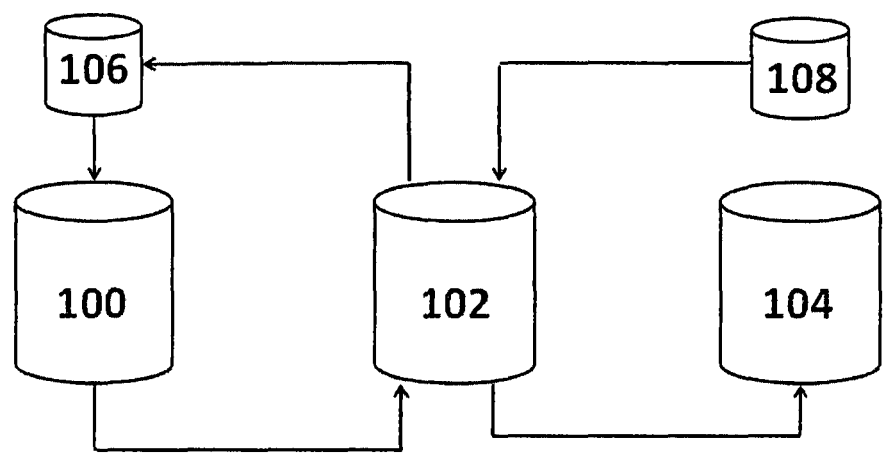
FIG. 16 depicts the integrated scheme for the conversion of fructose to FDCA.

FIG. 16 shows the integrated scheme for the conversion of fructose to FDCA. Reactor 100 is where the dehydration reaction occurs. Fructose and the various starting reactants, particularly isopropanol and 5% mol HCl, are added into this reactor 100. The isopropanol is added from tank 106. Isopropanol from reactor 100 may be first evaporated to form an aqueous slurry after the dehydration reaction ends. This aqueous slurry containing the crude HMF may have residual traces of isopropanol. This aqueous slurry is then passed through a water extraction tank 102 where water is added from tank 108. The HMF is extracted with the water from the aqueous slurry leaving behind the impurities, namely humins which are not soluble in water. The isopropanol may be recovered from tank 102 and recycled into tank 106. The extracted purified HMF is then transferred to the catalytic oxidation tank 104 to be subjected to air bubbling in the presence of an oxidation catalyst. Optionally, a base may be added to tank 104. FDCA formed from the oxidation of HMF are isolated from the resultant mixture.

EXAMPLES

Non-limiting examples of the invention and a comparative example will be further described in greater detail by reference to specific Examples, which should not be construed as in any way limiting the scope of the invention.

Materials

D-Fructose was from Alfa Aesar. 5-hydroxymethylfurfural (HMF) and 2,5-furandicarboxylic acid (FDCA) were purchased from Sigma-Aldrich. Dry isopropanol and hydrogen chloride (37%) were purchased from Merck. All the chemicals were used directly without any pre-treatment. Au/HT catalyst (hydrotalcite supported gold nanoparticles) was prepared as described below. The Pt/C catalyst (5 wt %) was from Aldrich.

Preparation of Au/HT and $Au_8Pd_2$/HT Catalyst

Au/HT catalyst was prepared by known deposition-precipitation method using $NH_3$ aqueous solution followed by calcination at 473 K (about 199.9° C.).

$Au_8Pd_2$/HT catalyst was also prepared using the above method. 0.1 mmol of $HAuCl_4$ and 0.025 mmol of $NaPdCl_4$ were dissolved in 40 ml water. To this solution, hydrotalcite (1 g) was added, followed by addition of $NH_3$ aqueous solution (29.5%, 0.425 mL) until pH 10 was reached. The solution was vigorously stirred for 6 h and refluxed for 30 min at 373 K (about 99.9° C.). The resulting solid was filtered, washed thoroughly with water, and heated at 473 K (199.9° C.) overnight.

Reaction Procedure for Producing HMF from Fructose

In a 8 ml thick wall sealed glass tube, 2.5 mmol fructose (0.45 g), 4.85 ml water-free isopropanol, 0.15 ml water (3 vol %), and 10 ul 37% HCl (5 mol %) were added. This solution was purged thoroughly with argon gas for 3 times to remove all possible presence of air. Under magnetic stirring at 700 rpm, the reaction was heated to 120° C. in oil bath for 3 hours. After the reaction, the solution was cooled down using an ice bath. The solution was then diluted in water for HPLC testing. For 1 mmol and 5 mmol of fructose as starting materials, the experiment was conducted in 4 ml and 15 ml sealed glass tube, respectively. The addition of 0.15 ml water is not for dissolving the HCl. This small amount of water serves to increase HMF yield. Notably, water is miscible with isopropanol and forms a single phase solvent system.

Reaction Procedure to Produce HMF from JAT

In a 8 ml thick wall sealed glass tube, 0.3 g dried JAT powder (equivalent to 1.25 mmol fructose), 1.2 ml 0.25 M HCl saturated with NaCl, 4 ml MIBK were added. The solution was purged thoroughly with argon gas 3 times until all the air was removed. Under magnetic stirring at 700 rpm, the reaction was heated to 180° C. in a heating block for 30 minutes. After the reaction, the solution was cooled down with ice and centrifuged. The MIBK layer was taken out for further usage.

Figure 1:
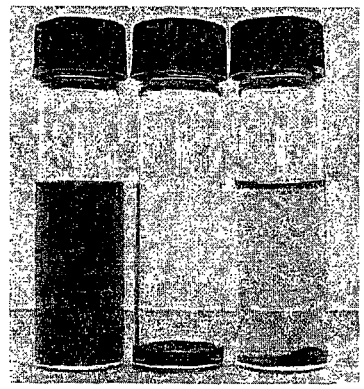
FIG. 1 depicts an as synthesized HMF isopropanol solution (left vial), raw HMF product after evaporation of solvent (middle vial) and HMF re-dissolved in water (right vial).
Figure 2:
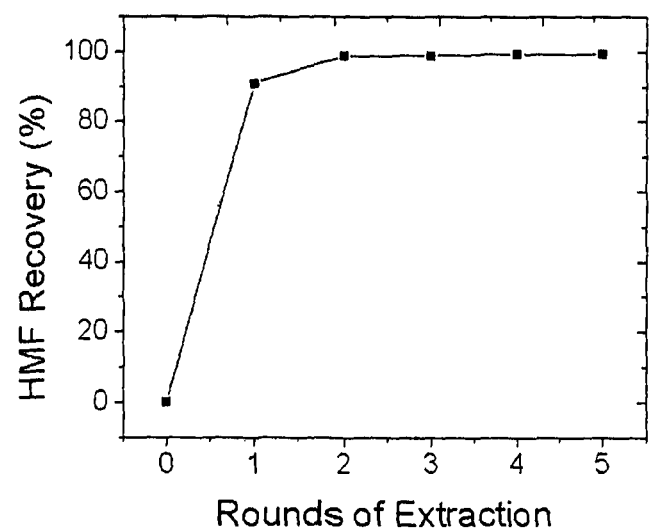
FIG. 2 depicts a plot of the number of extraction against the HMF recovery rate.

Procedure to Purify HMF Via Water Extraction 1 mmol of HMF original solution in isopropanol was evaporated (90 mbar, 40° C.). The evaporation was completed before adding water for extraction. A dark brown thick liquid of raw HMF product was obtained. 5 ml of water was then added and centrifuged until the dark impurities detached from the water solution and collect as a residue at the bottom and along the bottle's wall. The solution bottle from each of these steps is shown in FIG. 1. The transparent yellowish supernatant was extracted and the black impurities remained on the surface of bottle wall. Another 5 ml of water was put in and rotated for another 15 min and the supernatant was collected. The collected solution was mixed and centrifuged to remove residue, if any, and a transparent yellowish solution was obtained. This water extraction process is very efficient and 99% of HMF was recovered within two rounds of extraction (see FIG. 2). This solution was used for further reaction.

Catalytic Reaction of HMF to FDCA

For this reaction, $Na_2CO_3$ was used as the base. 1 g of extracted HMF was first dissolved in 5 g of water. The $Na_2CO_3$ was separately prepared by dissolving $Na_2CO_3$ in water. The oxidation catalyst was then added follow by the HMF solution at ambient room temperature. With oxygen gas bubbling, the solution was first heated to 50° C. for 2 hours, and HMF was fully converted to HFCA. After that, the reaction was heat to 95° C. and kept for 7 hour. The pH of the aqueous solution was then adjusted to 1 and FDCA was precipitated from the solution. The precipitate was filtered and washed with ethanol.

Product Analysis

HMF and FDCA were analyzed by HPLC (Agilent Technologies, 1200 series) and its isolation yield further ascertained the presence. The isolation yield was obtained by weighing the FDCA product after it was separated from the HMF. The HPLC working conditions are: column (Agilent Hi-Plex H, 7.7×300 mm, 8 μm), solvent 10 mM $H_2SO_4$, flow rate 0.7 ml/min, 25° C., UV detector at 280 nm for HMF and 254 nm for FDCA. The retention times for detected compounds were 20.7 min, 24.4 min, 29.4 min and 36.5 min for FDCA, HFCA, FFCA and HMF, respectively. Fructose was measured using a Sugar Analyzer (DKK-TOA Corporation, Japan. Model: SU-300).

Characterization

Figure 6:
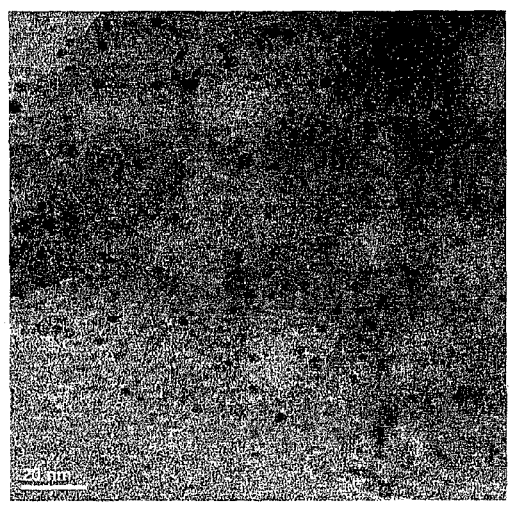
FIG. 6 is a TEM image showing the synthesized Au/HT catalyst.
Figure 7:
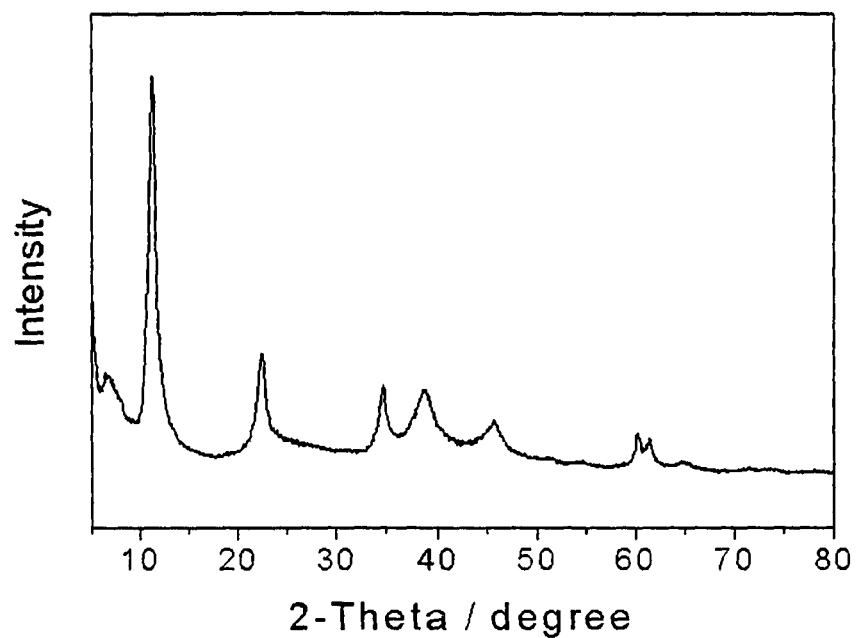
FIG. 7 shows the X-ray diffraction of the synthesized Au/HT catalyst.
Figure 8:
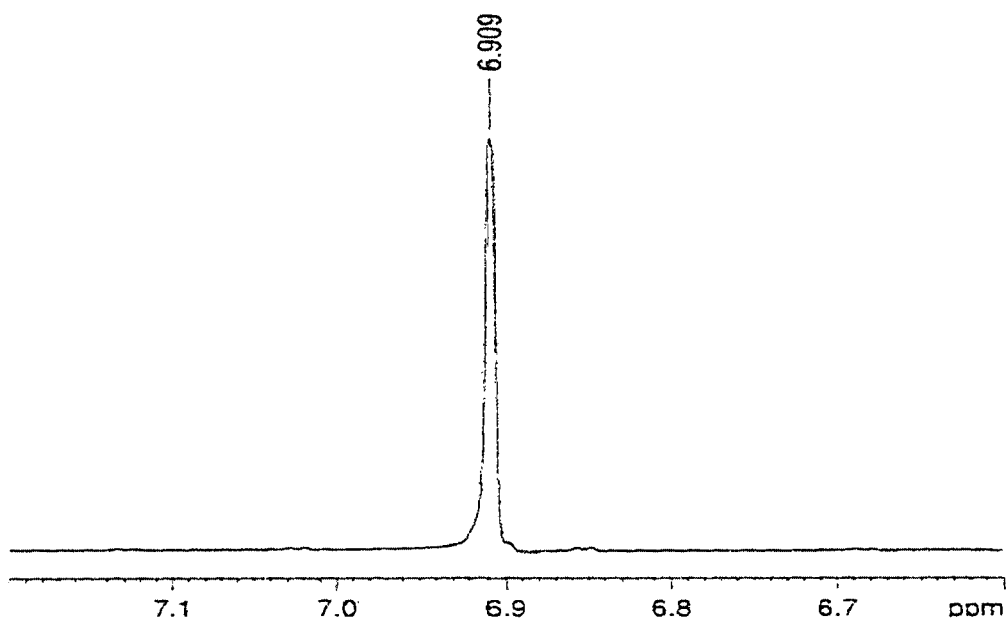
FIG. 8 depicts a H NMR spectrum of the isolated FDCA product.

The FDCA product was characterized by $^1H$ and $^{13}C$ NMR (Brucker AV-400). The synthesized Au/HT catalyst was characterized by TEM (FEI Tecnai F20) and XRD (PANalytical x-ray diffractometer, X'pert PRO, with Cu Kα radiation at 1.5406 Å). These TEM, XRD and NMR spectra are depicted in FIGS. 6 to 8.

Comparative Example 1

Complete removal of the organic solvent from the HMF solution serves as a key to achieving high quality HMF. This was done by first evaporating isopropanol from the original HMF solution at 90 mbar and 40° C., followed by evaporation at lower vacuum conditions (using a continuous evaporation mode of a rotary evaporator) to completely remove the organic solvent.

Without the latter step, the trace amount of isopropanol that remains in the crude HMF will introduce noticeable impurities to the subsequent water extraction solution, thereby producing a darker coloured aqueous solution and a slower catalytic reaction of HMF to FDCA occurs.

Complete evaporation of the organic solvent may also be achieved by first evaporating isopropanol from the original solution of HMF at 90 mbar and 40° C., and subsequently leaving the crude HMF to dry in air overnight.

An alternative experiment was also performed by first mixing an equal volume of water with the HMF isopropanol solution. The isopropanol is then evaporated from the solution. After removing the impurities from the aqueous solution by either filtration or centrifuge, more than 99% of the HMF remained in the water solution. However, more dark impurities also appeared in the aqueous solution. This may be due to the presence of a small amount of isopropanol which remained in the solution and therefore more impurities are dissolved in the liquid phase. Hence, it would advantageous to completely evaporate the organic solvent used for the dehydration reaction before adding water for extraction. Otherwise, the remaining solution would contain a higher amount of impurities.

Comparative Example 2

The use of active carbon absorbents have been carried out so as to understand the purification yield through this method.

Figure 9:
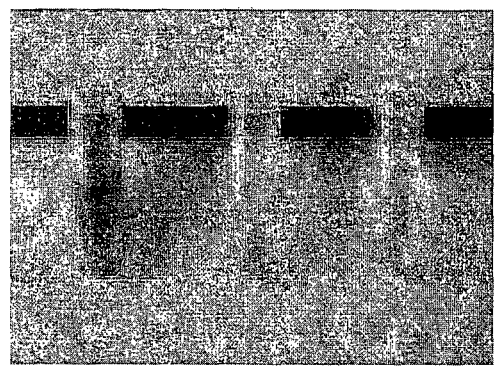
FIG. 9 depicts HMF treated with 0.1 g of active carbon (left eppendorf tube), HMF treated with 1.0 g of active carbon (middle eppendorf tube) and a purified aqueous solution of HMF in water (right eppendorf tube).

Table 1 below shows the various HMF recovery percentages using different amount of active carbon. A pure HMF solution has a characteristic clear pale yellow colour (as denoted by the lighter shade of the solution in the right eppendorf tube of FIG. 9). Although using 0.1 g of active carbon provides a higher HMF recovery of 88% as compared to 1 g of active carbon which has only a 49% recovery yield, the solution colour obtained for the latter was a yellowish clear solution (see center eppendorf tube of FIG. 9, as denoted by a darker shade relative to the solution contained in the right most eppendorf tube of FIG. 9) compared to the earlier which had a dark brown appearance containing traces of impurities (see left eppendorf tube of FIG. 9, as denoted by the darker shade relative to the other two eppendorf tubes).

TABLE 1

| HMF recovery using different amount of active carbon | |
|---|---|
| Type of HMF Solution | HMF recovery |
| 1 mmol HMF treated with 0.1 g active carbon | 88% |
| 1 mmol HMF treated with 1 g active carbon | 49% |
| Pure HMF solution | Not applicable |

From this study, active carbons are not as effective as water extraction which allows up to more than 98% recovery yield as illustrated in comparative example 3.

Comparative Example 3

HMF before and after purification have been tested in the oxidation reaction with Au/HT or Pt/C catalyst. As shown in trial 1 and 2 of table 2 below, reactions with un-purified HMF all encountered catalyst deactivation problem as observed from its lower FDCA yield. Consequently, a mixture product comprising HFCA and FDCA was obtained as final product (see FIG. 3 step 100). Even with an extended reaction time of 20 hours, no improvement was observed.

However, for the water extracted HMF, the reaction was completed in 7 hours for Au/HT catalyst and 4.25 hours for Pt/C catalyst, and more importantly, only FDCA having a yield of more than 98% was detected as the final product (see FIG. 3 step 102).

As $Na_2CO_3$ was used as the base for this catalytic oxidation, no obvious leaching of $Mg^{2+}$ from the hydrotalcite (HT) support in the Au/HT catalytic system was observed. Leaching is also avoided when NaOH is used. If no base is used, FDCA as an acid, will react with HT to form FDCA Magnesium salt.

TABLE 2

| Oxidation of HMF to FDCA | | | | |
|---|---|---|---|---|
| Trial | HMF | Catalyst | Time (hours) | FDCA Yield |
| 1 | No Water Extraction | Au/HT | 20 | 39% + HFCA |
| 2 | No Water Extraction | Pt/C | 20 | 51% + HFCA |
| 3 | Water Extracted | Au/HT | 7 | 99% |
| 4 | Water Extracted | Pt/C | 4.25 | 98% |

For trials 1 and 3, an aqueous solution containing 1 mmol of HMF in 10 ml $H_2O$ was used. Amount of Au/HT catalyst used was 0.25 g. The ratio of HMF to Au is 40 mol/mol. Oxidation was carried out under 1 mmol $Na_2CO_3$ with $O_2$ bubbling at a temperature of 50° C. for the first 2 hr followed by 95° C. for the remaining 18 hours.

The conditions of trials 2 and 4 are 10 ml $H_2O$, 0.4 g Pt/C Catalyst, HMF/Pt of 10 mol/mol, 0.5 g NaOH. For these trials, 1 mmol of HMF in 5 ml $H_2O$ was added dropwise under $O_2$ bubbling at 25° C.

Figure 10:
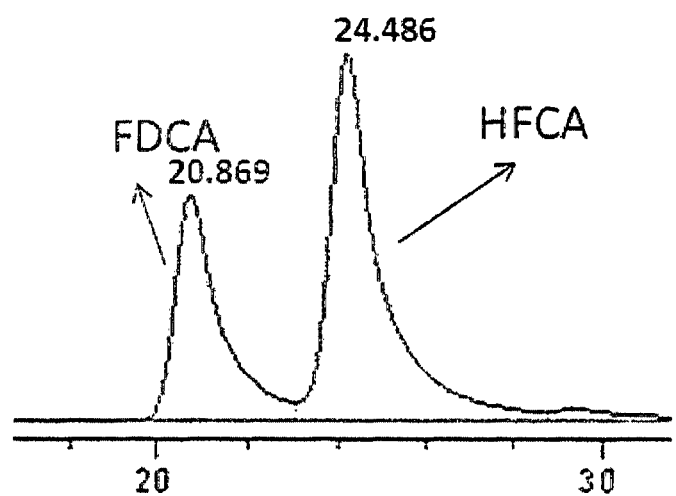
FIG. 10 shows the HPLC testing results for the conversion of HMF to FDCA using Au/HT catalyst without purification for 20 h at 95° C.
Figure 11:
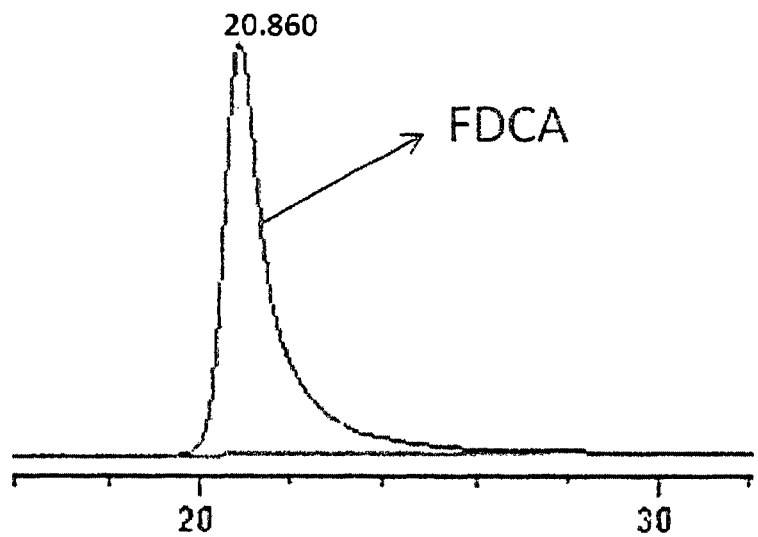
FIG. 11 shows the HPLC testing results for the conversion of purified HMF to FDCA using Au/HT catalyst for 7 h at 95° C.

The HPLC product analysis for trials 1 and 3 are shown in FIGS. 10 and 11. When catalyst deactivation occurs due to impurities such as humins, dual FDCA and HFCA peaks are observed in FIG. 10. Only a single FDCA product peak was observed in FIG. 11 for the water extracted HMF.

Comparative Example 4

Figure 12:
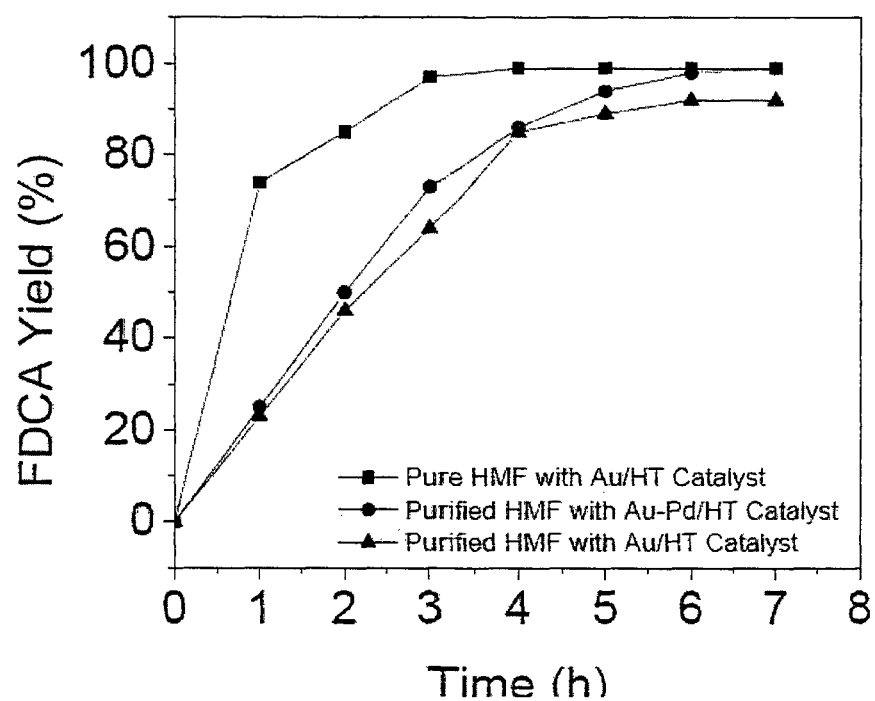
FIG. 12 shows the kinetic studies of converting commercially pure HMF (pure HMF) and purified HMF (water extracted fructose-derived HMF) to FDCA using different catalysts.

Kinetic Studies were conducted for oxidation of both commercial HMF and water extracted purified HMF using Au/HT catalyst under the same reaction conditions (1 mmol HMF in water together with catalyst and $Na_2CO_3$, aliquot of solution was taken out every hour for HPLC measurements) (see FIG. 12).

The conversion of purified HMF to FDCA obtained from natural fructose was completed within 7 hours. This was slightly slower than the conversion using commercial HMF which finished in 4 hours (see FIG. 12). After further investigation, the optimum reaction conditions for the purified HMF were determined as follow.

The reaction mixture was first kept under oxygen gas at 50° C. for 2 hours, in which most of the HMF was converted to HFCA. The reaction temperature was then raised to 95° C. for another 7 hours in which all the HFCA was fully converted to FDCA with a yield up to 99%.

Alternatively, kinetic study for a palladium-modified gold catalyst ($Au_8Pd_2$/HT) using water extracted HMF is also demonstrated (see FIG. 12). This $AU_8Pd_2$/HT catalyst was capable of converting purified HMF to FDCA in 7 h with 95% to 99% yield at 95° C. without the need for pretreatment at a lower temperature of 50° C. for 2 h (see FIG. 12).

Figure 4:
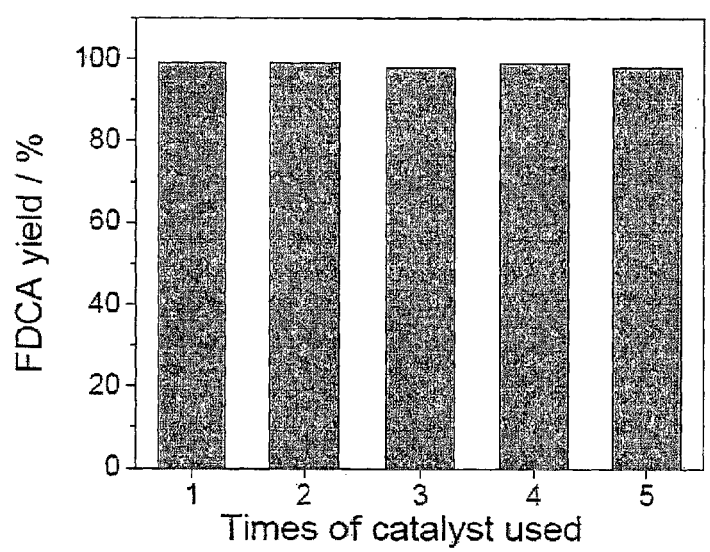
FIG. 4 shows a plot of the FDCA yield against the number times the $Au_8Pd_2$/HT catalyst is recycled.
Figure 14:
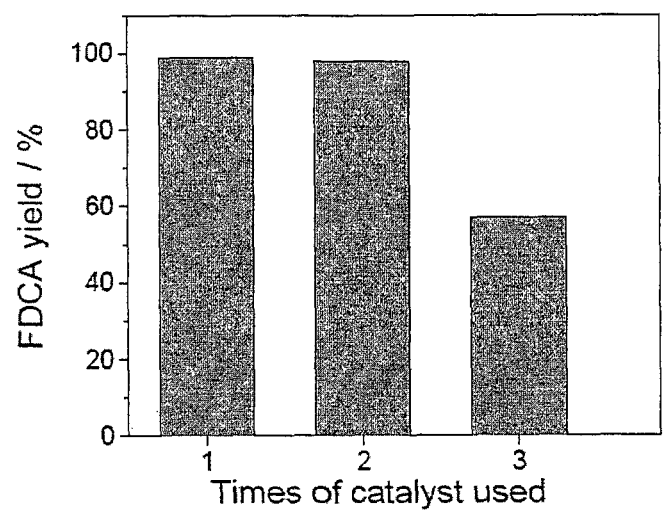
FIG. 14 shows the Au/HT recyclability test with purified HMF via water extraction.
Figure 15:
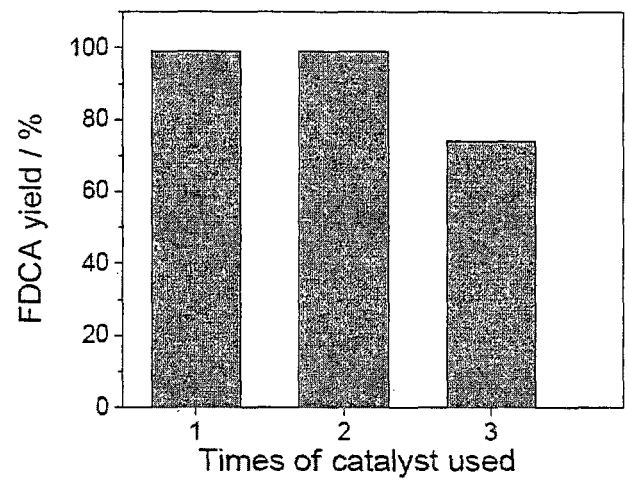
FIG. 15 shows the Au/HT recyclability test with pure HMF from Aldrich.

The tolerance of Au/HT catalyst for this biomass-based HMF was also studied. The Au/HT catalyst showed high activity for the first 2 runs with an FDCA yield of 98-99% (see FIG. 14). However from the 3rd run, a significant slowdown of reaction speed was observed (about 56%). In a parallel experiment with pure HMF (from Aldrich) as the starting material, a lower reaction speed of 78% was also observed for the 3rd run (see FIG. 15). To increase the durability of the catalyst, we have prepared palladium-modified Au/HT ($Au_8Pd_2$/HT) as a new catalyst, which showed excellent recyclability. The catalyst was kept at high activity for at least 5 runs with FDCA yield of 98% to 99% (see FIG. 4), using the purified HMF from fructose. The same conditions for each run are used. This conditions are 1 mmol of HMF, 1 mmol $Na_2CO_3$, 10 ml $H_2O$, 0.25 g Au/HT, $O_2$ bubbling, and 50° C. for the first 2 h followed by 95° C. for the next 7 h.

Integration of Dehydration and Oxidation

Since we have successfully demonstrated the conversion from fructose to HMF in isopropanol and the purification of HMF by water extraction, followed by oxidation of HMF to FDCA, we have also experimented with the integration of these two processes that was previously considered to be incompatible.

The two step reactions were integrated together for the direct conversion of fructose to FDCA. In this process, fructose was converted to HMF in isopropanol with 5 mol % of HCl as catalyst. After the reaction, the isopropanol was separated by evaporation and collected for the next run reaction. Then, HMF was extracted with water and this aqueous solution was directly used for the oxidization reaction. As shown in table 3 below, an overall 83% FDCA yield was achieved. During this integrated process, both solvent (isopropanol) and catalyst (Au/HT) can be recycled. The whole process did not produce any additional waste and only water was consumed during HMF purification process. Hence, it goes to show that water extraction of HMF allows FDCA from fructose to be produced in an environmentally benign manner via an integrated process that is very efficient and cost effective.

TABLE 3

Integrated process from Fructose to FDCA

| Trial | Fructose (mmol) | HMF HPLC Yield | HMF Isolated Yield | FDCA Yield |
|---|---|---|---|---|
| 1 | 1 | 85.3% | 84% | 83% |
| 2 | 5 | 80.2% | 79.4% | 78% |

The reaction conditions for trial 1 are 19.4 ml of isopropanol, 0.06 ml of $H_2O$, 0.05 mmol of HCl, 120° C. for 3 hours. Trial 2 is a scaled up of the experiment by 5 times.

The reaction conditions for trial two are based on having the HMF in trial 1 extracted using 10 ml of $H_2O$. Subsequently, oxidation to FDCA was carried out using 0.25 g of Au/HT, 1 mmol of $Na_2CO_3$, $O_2$ bubble, 50° C. for 2 hours followed by 95° C. for 7 hours.

It should be noted that the FDCA yield is the isolated overall yield based on fructose. An isolated yield refers to one where the product has been separated or isolated, and then weighed. Although this involves more effort, such an isolated yield is considered as the absolute yield. On the other hand, a HPLC yield (not the HPLC isolated yield) is a relative yield and not an absolute yield as the product is not isolated before it is being weighed to determine the yield.

Water Extraction of HMF Derived from Biphasic Systems

As disclosed above, the crucial step for converting HMF to FDCA completely relies on the use of water to extract and purify HMF. This method not only removes impurities in a cost-effective manner but also generates HMF aqueous solution that can be directly used for the next step catalytic oxidation step. This purification method can be easily incorporated into any mass production processes for FDCA or other processes as demonstrated above. Relying on this, we have also experimented using HMF derived from biphasic systems. Biphasic dehydration solvent systems are widely utilized for HMF production from fructose, glucose or cellulose.

To test the integrated process for the conversion of fructose to FDCA using biphasic fructose dehydration method, a MIBK/water biphasic system was used. The water used for this dehydration system is not the extracting solvent.

Figure 13:
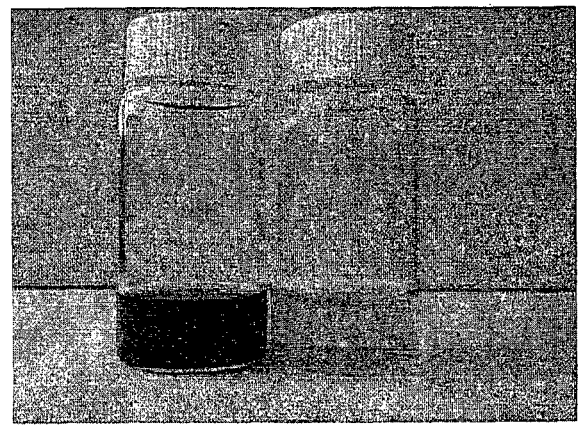
FIG. 13 depicts HMF prepared in water/MIBK biphasic system without purification (left vial), and after purification and dissolved in water (right vial).

After dehydration, HMF product (about 55% yield) present in the organic MIBK layer was dried and extracted with water. This was directly used for oxidization reaction to FDCA. The difference between HMF extracted with water and one that was not extracted with water is shown in FIG. 13. The left vial shows a dark colour solution having HMF not extracted with water (it should be noted that this solution is brown in colour which is characteristic of crude HMF co-existing with impurities). The right vial shows water extracted HMF.

Under standard oxidation conditions (oxygen bubbling, $Na_2CO_3$ as base, solution first heated to 50° C. for 2 h to fully convert HMF to HFCA, followed by further reaction to FDCA at 95° C. 7 h), an FDCA yield of more than 97% with 100% HMF conversion was achieved.

HMF prepared from glucose in a biphasic system of water/THF using $HCl/AlCl_3$ as catalyst produced a HMF yield of 52%. For this as-prepared HMF in THF solution, with water extraction, more than 99% of HMF was recovered after purification and the final overall FDCA yield was 50%.

The above demonstrated that a water extraction HMF purification method can be applied in different processes for the conversion of biomass to FDCA, even with different feed materials.

Figure 5:
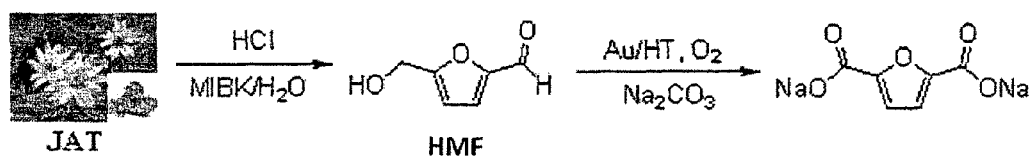
FIG. 5 shows the integrated process for the conversion of JAT biomass to FDCA.

For further illustration, the conversion of Jerusalem Artichoke (JAT) biomass to FDCA was tested using the MIBK/water biphasic system for dehydration and the Au/HT catalyzed oxidization reaction (see FIG. 5). JAT is an abundant, easy and fast growing biomass with very high inulin/fructose component (about 68 to 83% fructans). Compared to the monophasic system, the biphasic system works better for the conversion of JAT to HMF/FDCA as impurities in JAT, such as biomolecules (proteins, DNA, RNA, vitamins), ions (Na+, K+, Mg2+, Ca2+, Fe3+), fibers and gels, tend to remain in the water layer. The HMF is extracted to MIBK, making the HMF purer. After the reaction, the crude HMF in MIBK was evaporated to remove MIBK for reuse, and the raw HMF was purified with the currently disclosed water extraction method to obtain a light colored aqueous solution (this is yellow in colour due to the HMF). The HMF aqueous solution was then used as feedstock for the Au/HT-catalyzed oxidization reaction.

In this process, HMF was produced with 57% yield in the first step (not optimized) and the overall yield for FDCA was 55% (based on the fructose component in JAT).

Applications

The disclosed method provides an efficient and cost-effective water extraction method for purifying an optionally substituted furan which may be obtained after dehydrating a biomass.

Advantageously, water is an environmentally benign solvent as compared to other organic solvents used in conventional mono-phase or biphasic dehydration reactions.

Advantageously, by evaporating the organic solvents used in the dehydration reaction and adding water subsequently to extract the intermediate optionally substituted furan, deactivation of downstream catalyst used for oxidation is avoided.

Accordingly, up to 99% of the HMF could be recovered and the HMF aqueous solution could be directly used for further catalytic oxidation reaction to convert to FDCA as the sole product.

The disclosed method also overcomes the limitations of multiple extraction processes which consume more solvent, column chromatography or HPLC processes which are unsuitable for mass production and active carbon absorbents which do not produce a sufficiently high purification yield.

The disclosed method also allows the direct conversion of a biomass to an optionally substituted furoic acid since the dehydration step and oxidation step may be integrated through the incorporation of a water extraction process. An integrated process from fructose to FDCA attained an overall FDCA yield of 83%.

Holistically, the method disclosed enhances the purification yield of the intermediate optionally substituted furan and the conversion yield of the resultant optionally substituted furoic acid.

By using the disclosed method, a purified aqueous solution of the optionally substituted furan, particularly HMF may be obtained. This purified aqueous solution can be subjected to downstream processing for producing other polymers without the need for further complex purification processes. Due to the advantageous features, the methods as disclosed above may be scaled up to industrial processes.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

What is claimed is:

1. A method for synthesizing an optionally substituted furoic acid, comprising:
   converting a biomass to an optionally substituted furan, wherein said furan is unsubstituted or substituted by at least one —$C_1$-$C_{10}$-alkyl-OH group, via a dehydration reaction in the presence of an organic solvent;
   purifying the optionally substituted furan by first evaporating the organic solvent from the optionally substituted furan produced from said dehydration reaction to obtain a solid residue or an aqueous slurry, followed by adding water to the residue or aqueous slurry for extraction of the optionally substituted furan with water, collecting the supernatant separately from the residue; and
   oxidizing the extracted optionally substituted furan to form the optionally substituted furoic acid.

2. The method according to claim 1, wherein the water extraction is repeated several times and the extracts containing the optionally substituted furan are combined.

3. The method according to claim 1, wherein said dehydration reaction is an acid catalyzed dehydration reaction.

4. The method according to claim 1, wherein said optionally substituted furan is 5-(hydroxymethyl)furfural.

5. The method according to claim 1, wherein said organic solvent is selected from the group consisting of alcohols, ketones, tetrahydrofuran, γ-valerolactone and mixtures thereof.

6. The method according to claim 5, wherein the organic solvent is selected from the group consisting of isopropanol, 1-butanol and methyl isobutyl ketone.

7. The method according to claim 5 which comprises an ionic liquid as the co-solvent used in the dehydration reaction.

8. The method according to claim 1, wherein the oxidization of the optionally substituted furan is carried out in the presence of oxygen, a catalytic system and optionally a base.

9. The method according to claim 8, wherein said catalytic system is a supported catalytic system comprising gold/hydrotalcite, gold-palladium/hydrotalcite or platinum/carbon.

10. The method according to claim 8, wherein said catalytic oxidation is carried out for about 1 to 3 hours at about 30 to 70° C.

11. The method according to claim 8, wherein said catalytic oxidation is further carried out for 4 to 10 hours at 80 to 110° C.

12. The method according to claim 1, wherein said biomass is Jerusalem artichoke.

13. The method according to claim 1, wherein said biomass comprises a carbohydrate.

14. The method according to claim 1, wherein said optionally substituted furoic acid is 2,5-furandicarboxylic acid.

15. The method according to claim 1, wherein said optionally substituted furoic acid is 5-hydroxymethyl-2-furancarboxylic acid.

16. The method according to claim 2, wherein the water extraction is repeated for 2 to 3 times.

17. The method according to claim 3, wherein said acid catalyzed dehydration reaction occurs in the presence of a mono-phase solvent system or a biphasic solvent system.

18. The method according to claim 5, wherein the organic solvent is isopropanol.

19. The method according to claim 7, wherein said ionic liquid is water.

20. The method according to claim 13, wherein said carbohydrate is selected from the group consisting of cellulose, fructose and glucose.

* * * * *